United States Patent
Yoo et al.

(10) Patent No.: US 6,492,163 B1
(45) Date of Patent: Dec. 10, 2002

(54) CELL CULTURE TUBE AND MULTIPLE ROLLER TUBE CELL CULTURE SYSTEM USING THE SAME

(75) Inventors: Kwang Hyun Yoo, Yongin (KR); Wan Kyu Choi, Yongin (KR); Sung Ho Shin, Cheongju (KR)

(73) Assignee: Core Biotech Co., Ltd. (KR)

( * ) Notice: Subject to any disclaimer, the term of this patent is extended or adjusted under 35 U.S.C. 154(b) by 0 days.

(21) Appl. No.: 09/956,172

(22) Filed: Sep. 19, 2001

(30) Foreign Application Priority Data

May 21, 2001 (KR) ......................................... 2001-27831

(51) Int. Cl.⁷ .......................... C12M 1/00; C12M 1/24; C12N 11/14
(52) U.S. Cl. ................... 435/298.2; 435/176; 435/182; 435/395; 435/394; 435/304.1; 435/809
(58) Field of Search ............................... 435/176, 182, 435/394, 395, 298.2, 304.1, 809

(56) References Cited

U.S. PATENT DOCUMENTS

| | | | |
|---|---|---|---|
| 3,827,943 A | * 8/1974 | Mann | 435/298.2 |
| 4,144,136 A | * 3/1979 | Corbeil | 435/298.2 |
| 4,220,725 A | 9/1980 | Knazek et al. | 435/285 |
| 4,238,568 A | * 12/1980 | Lynn | 215/10 |
| 4,310,630 A | 1/1982 | Girard et al. | 435/284 |
| 5,064,764 A | 11/1991 | Besnainon et al. | 435/285 |
| 5,132,090 A | * 7/1992 | Volland | 261/87 |
| 5,728,577 A | * 3/1998 | Kuriyama | 210/150 |

* cited by examiner

*Primary Examiner*—David A. Redding
(74) *Attorney, Agent, or Firm*—Madson & Metcalf (57) ABSTRACT

A cell tube for ex vivo culturing animal cells and a multiple roller tube cell culture system are disclosed. Suitable for use in culturing cells, the tube has at its opposite end walls two openings through which culture media can come in and out. The openings are eccentrically located at corresponding positions in contact with the edge sides of the end walls. The system has a plurality of roller drums on which a multitude of cell tubes are assembled. As the roller drums are rotated, cells adhering to each tube experience a nutrient-rich state and aerobic starvation, repeatedly. In the nutrient-rich state, the cells are grown flourishingly. When subjected to starvation, cells select metabolism pathways for utilizing carbon sources effectively, produce lactate at a low rate and can maintain a constant pH, because they are in direct contact with air. The system makes cells adhere to the wall of cell tubes and provides air directly to cell surfaces. Adherent cells can be grown with normal morphology at high yield for a long time in the cell culture system. The cell culture can be easily scaled up simply by increasing the number of the roller drums. The system can exchange media and feed a gas mixture of oxygen and carbon dioxide easily, thus providing optimal environments suitable for small to large scale cell culture.

14 Claims, 9 Drawing Sheets

CELL CULTURE TUBE AND MULTIPLE ROLLER TUBE CELL CULTURE SYSTEM USING THE SAME

BACKGROUND OF THE INVENTION

1. Field of the Invention

The present invention relates, in general, to a tube suitable for use in ex vivo culturing of animal cells and a multiple roller tube cell culture system using the same and, more particularly, to a cell tube having at its opposite end walls two eccentric openings through which culture media can flow in and out. Also, the present invention is concerned with a multiple roller tube cell culture system using a multitude of cell tubes, which is able to culture adherent cells in a continuous or batch type manner with high efficiency.

2. Description of the Prior Art

Conventionally, it is difficult to grow ex vivo cultures of animal cells at high yield and in a concentrated level compared to microorganisms because animal cells which have weak cell membranes and are apt to undergo shear stress. The necessity for animal cell cultures has been increased for various reasons. Various efforts have been made to culture animal cells, but in most such efforts, culture methods for bacteria were applied to the cultures of animal cells irrespective of characteristics of animal cells. Thus, the success of the efforts was not great in spite of much investment.

As a result of recent advances in cell characterization, culture methods have been studied for various cells, especially ES (embryonic stem) cells, hybridoma cells, and CHO (Chinese hamster ovary). Highly concentrated cultures of lymphocyte lineage cells, of which hybridoma cells are representative, can be grown on a membrane by virtue of the development of the hollow fiber system of ASM company. Also, it is possible to culture ES and cancerous cells can be cultured in tissue slices as the rotary cell culture system developed by NASA ensures cell's undergoing low shear stress and provides environment control.

Cytokines or useful proteins are generally produced from transformed adherent cells, such as CHO, 3T3 or C127, by gene manipulation. The accomplishment of the human genome project allows the expectation that various useful proteins might be produced using adherent cells.

However, mass cultures of adherent cells to which fibroblasts and epithelial-like cells have not yet been developed completely. In fact, culture methods for ES cells or hybridoma cells are applied to the adherent cells, so that not only is the culture yield decreased significantly, but also the adherent cells cannot be cultured for a long time period.

SUMMARY OF THE INVENTION

It is an object of the present invention to overcome the problems, encountered in prior arts, of being unable to culture adherent cells for a long period of time and at high yield, and to provide a cell culture system in which adherent cells can be cultured with ease and high productivity.

It is another object of the present invention to provide a method for culturing animal cells on a large scale with high efficiency.

In accordance with an aspect of the present invention, there is provided a cell tube for use in culturing cells, having two openings through which culture media can flow in and out, the openings being eccentrically located on opposite end walls at corresponding positions in contact with the side edges of the end walls.

In accordance with another aspect of the present invention, there is provided a multiple roller tube cell culture system, comprising: one or more cell culture tube bundles, each consisting of a plurality of cell culture tubes axially arranged around the central rotating shaft within a cylindrical housing such that the eccentric opening formed on each end wall of each of the tubes is positioned outward in a radial direction of the housing; an air inlet and an air outlet formed on the housing for feeding oxygen to the interior of the housing; a level controller for maintaining a desired level of cell culture medium inside the housing; a medium inlet for feeding the cell culture medium to the interior of the housing; a plurality of sensors for sensing the pH and dissolved oxygen level inside the housing; and a harvest outlet for automatically discharging culture products from the housing after the cell culturing process is finished.

In accordance with a further aspect of the present invention, there is provided a method for culturing adherent animal cells on a large scale using the multiple roller tube cell culture system, comprising the steps of: feeding a predetermined amount of a culture medium into the cell culture system through the inlet by use of the medium transfer pump under the control of the level controller; rotating the roller drum on which cell tubes are assembled, at a speed of 1 rpm or less to repeatedly bring a portion of cell tubes into contact with the influent medium and air, the cell tube assembly being connected to the axis of the motor; controlling the pH and dissolved oxygen level of the cell culture with the aid of sensors; and increasing the rotation speed to 60 rpm or less to exchange the cell culture with a fresh medium and recover the cell culture.

DETAILED DESCRIPTION OF PREFERRED EMBODIMENTS

The application of the preferred embodiments of the present invention is best understood with reference to the accompanying drawings, wherein like reference numerals are used for like and corresponding parts, respectively.

Construction of the invention

Figure 1:
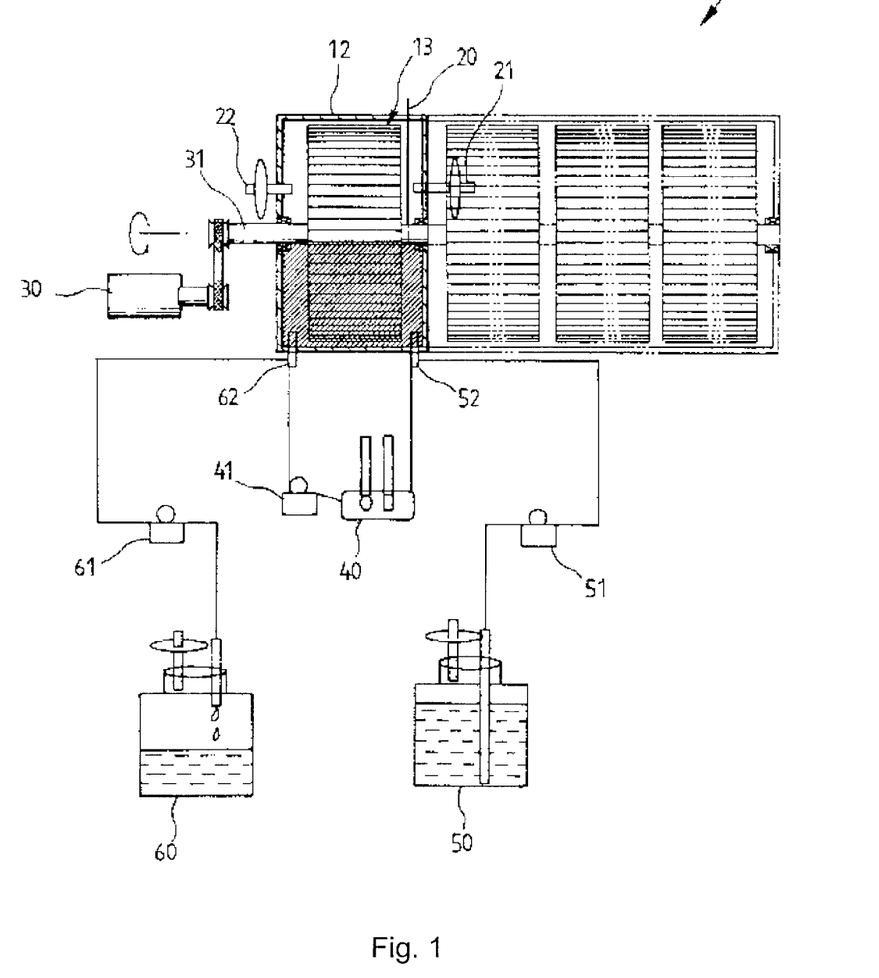
FIG. 1 is a diagram showing the structure of the multiple roller tube cell culture system of the present invention, which is equipped with a plurality of roller drums, each provided with a multitude of cell tubes.

FIG. 1 shows the construction of the multiple roller tube cell culture system 10 according to the present invention. In the cell culture system 10, a plurality of cell culture tubes 11 are closely and axially arranged around a central rotating shaft 31 within a cylindrical housing 12, thus forming a cell culture tube bundle 13. In such an arrangement, the eccentric openings 14 of the tubes 11 are positioned outward in a radial direction of the housing 12. One or more cell culture tube bundles 13 are integrated into a single unit to form a desired system 10. The rotating shaft 31 of the tube bundle 13 is connected to the output shaft of a drive motor 30 by a belt transmission mechanism, and rotated in conjunction with the motor 30. The housing 12 is provided with an air inlet 21 and an air outlet 22 for feeding oxygen to the interior of the housing 12 of the cell culture tube bundle 13. The system 10 also has a level controller 20 for maintaining a desired level of cell culture medium inside the housing 12. In addition, a medium transfer pump 51 feeds a predetermined amount of cell culture medium from a medium reservoir 50 to the interior of the housing 12 through a medium inlet 52 of the housing 12. The system 10 also has a plurality of sensors 40 for sensing the pH and dissolved oxygen level inside the housing 12 during a cell culturing process of the system 10. The system 10 also has a harvest outlet 61 on the housing 12 for automatically discharging the culture products from the housing 12 to a harvest reservoir 60 after the cell culturing process is finished.

Figure 2:
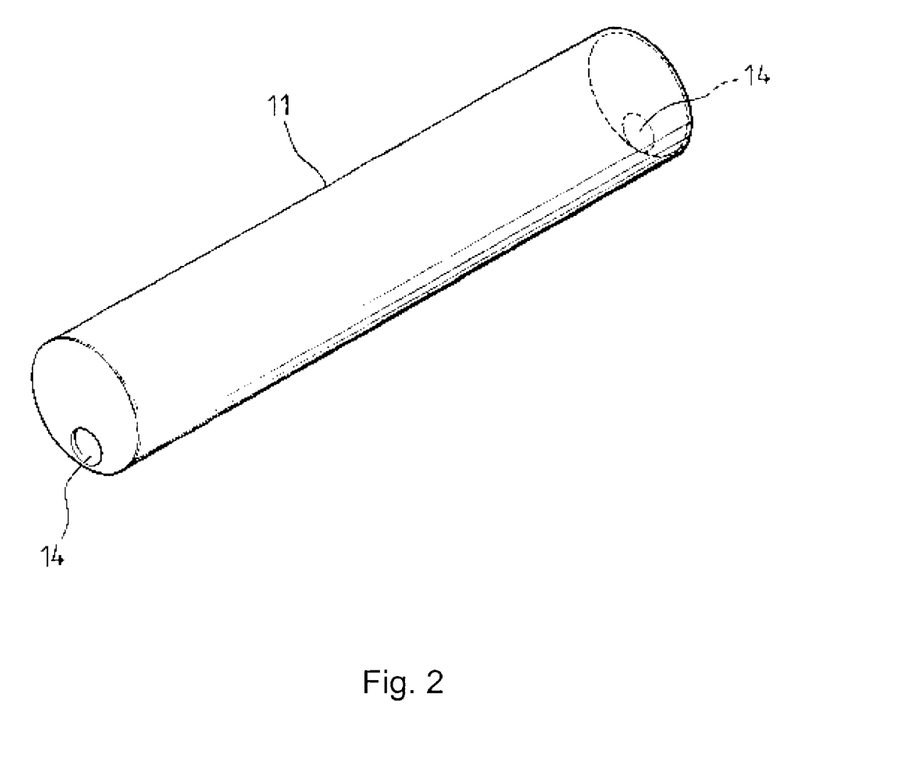
FIG. 2 is a perspective view showing the structure of the cell tube.

In the system 10, the opposite ends of each cell culture tube 11 are closed with end walls, but are provided with eccentric openings 14 at corresponding positions where the openings 14 are inscribed with the circular edges of the end walls. Therefore, the cell culture tubes 11 are almost free from interference or resistance of the medium during the flow of the medium relative to the tubes 11, thus being less likely to be ill-affected by shear stress and accomplishing a desired cell culturing process.

Figure 3:
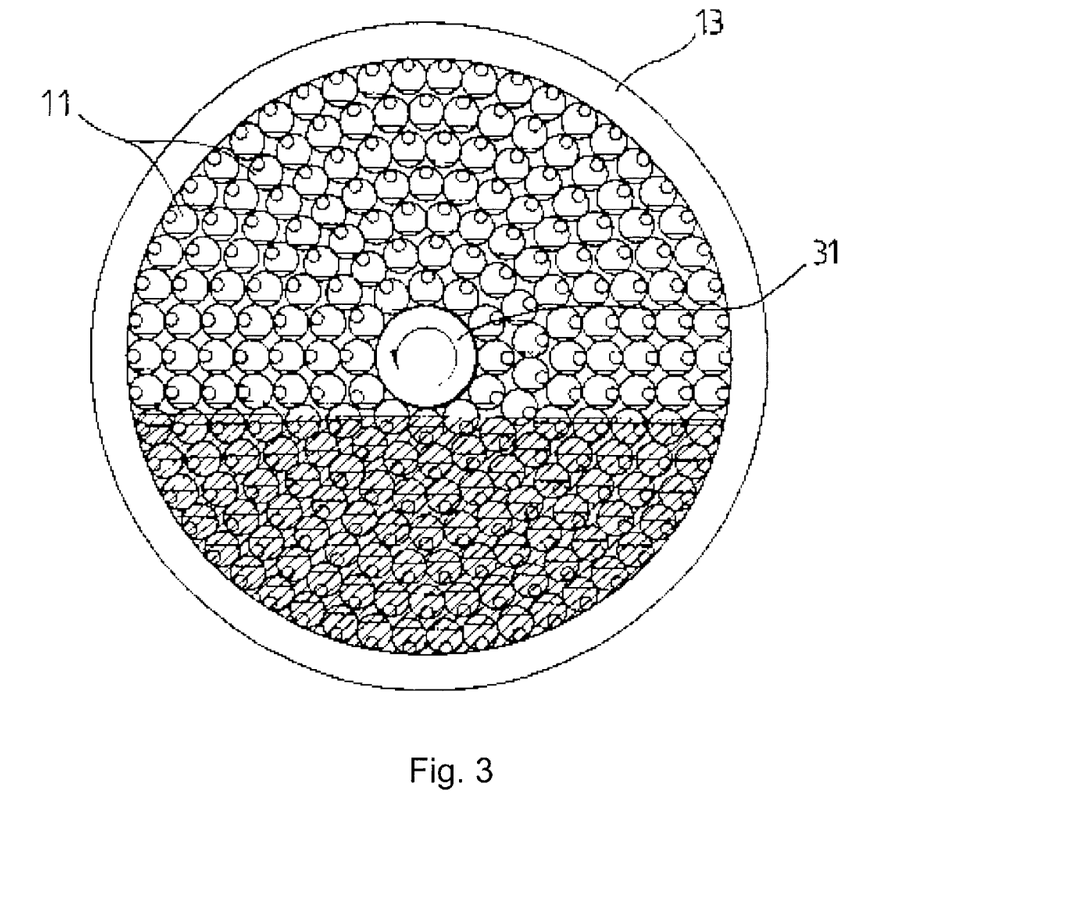
FIG. 3 is a cross sectional view showing a roller drum on which cell tubes are assembled.

In the cell culture system 10, a predetermined number of cell culture tubes 11 are closely and axially arranged around the rotating shaft 31 within a cylindrical housing 12 such that the eccentric openings 14 of the tubes 11 are positioned outward in a direction of centrifugal force of the housing 12. A cell culture tube bundle 13 is thus produced. One or more cell culture tube bundles 13 are arranged parallel to each other inside the system 10. Such a structure and arrangement of the cell culture tubes 11 is specifically designed to allow the cell culture medium to smoothly flow into or from the tubes 11, and is included in the gist of this invention.

In an operation of the system 10, a predetermined amount of cell culture medium is pumped from the medium reservoir 50 by the medium transfer pump 51 under the control of the level controller 20, and fed to the interior of the housing 12 through the medium inlet 52 of the housing 12, and so a predetermined level of the medium inside the housing 12 is continuously maintained. After the cell culturing process, the culture products are automatically discharged from the housing 12 to the harvest reservoir 60 by the harvesting pump 61. In addition, the ambient air as well as the pH and dissolved oxygen level inside the housing 12 are monitored by sensors 40 with circulation pump 41, and the sensors 40 automatically sense the state of the cultured cells.

During the cell culturing process of the system 10, a predetermined amount of humidified and sterilized air is continuously fed into the housing 12 through the air inlet 21, thus feeding oxygen to the cells. In such a case, gases are smoothly discharged from the housing 12 through the air outlet 22, thus maintaining a target oxygen level for the cells.

When the cell culture tubes 11 inside the housing 12 are rotated at a speed of ½ rpm or less around the central rotating shaft 31 by the rotating force of the motor 30, the cell culture tubes 11 are gradually sunk into the medium inside the housing 12. The medium is thus introduced into the cell culture tubes, and allows the cells to be stuck to the internal surface of the tubes and to grow in the tubes. The cells inside the culture tubes are induced to propagate by exposure to the media.

As described above, the cell culture tubes having the eccentric openings on their end walls are arranged around the rotating shaft inside the housing such that the openings of the tubes are positioned outward in the radial direction of the housing as best seen in FIG. 3. Therefore, when the tubes are rotated in a direction as shown in FIG. 3, the media contained in the housing smoothly flows into or from the tubes through the openings. In the present invention, the cell culture tubes may be arranged parallel to a direction of centrifugal force or inclined from the direction of centrifugal force at an angle of 0–10° to accomplish a desired flow of the medium relative to the tubes.

Figure 4A:
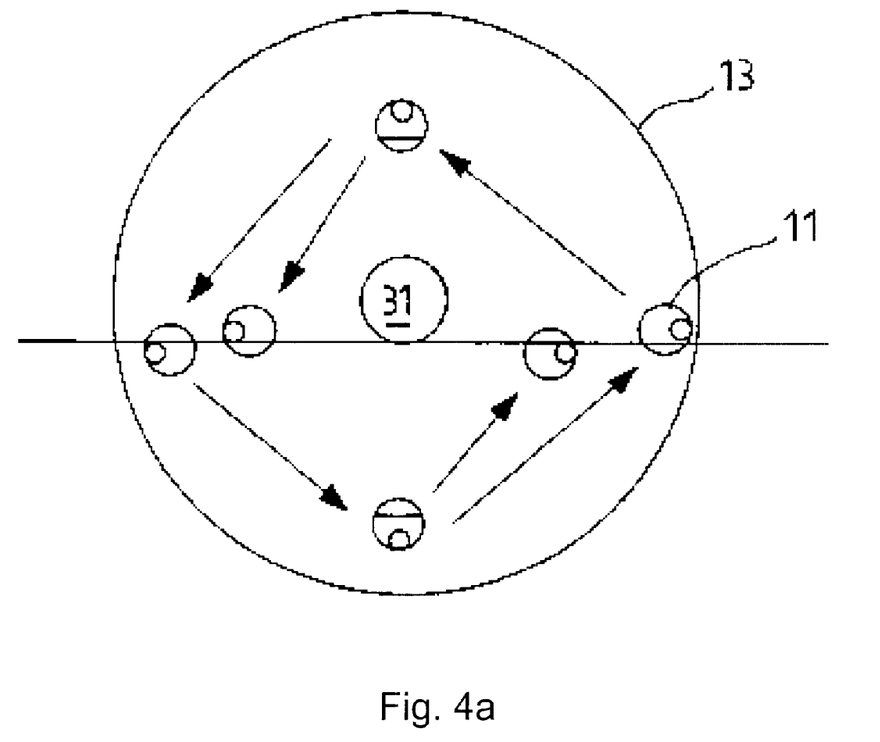
FIGS. 4a & 4b illustrates the inflow and outflow of medium of the cell tube during cell growth (a), and culture withdrawal (b), as it revolves around the axis.
Figure 4B:
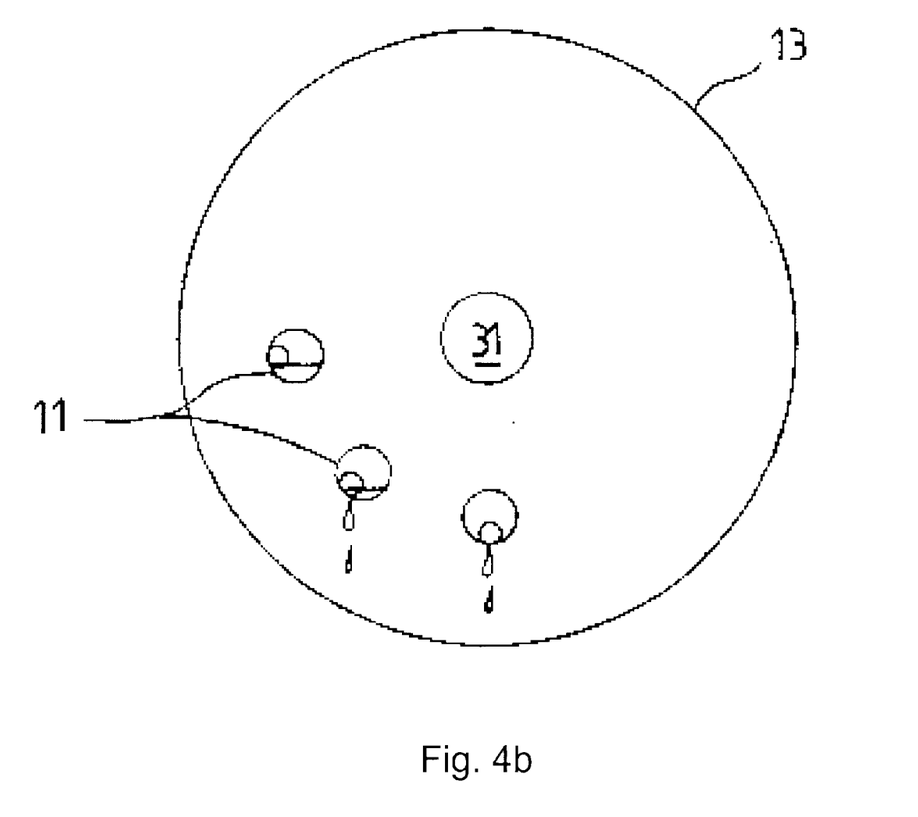

When cell floating liquid is introduced into the cell culture tube bundle as shown in FIG. 3, the complete attachment of the cells on the internal surface of the tubes necessarily requires 24–72 hours. When the cells are completely stuck to the internal surface of the tubes, the cell culture medium inside the tubes is distributed to the cells and changed with new medium as shown in FIGS. 4a and 4b. In addition, the cells inside the tubes are cultured with appropriate concentrations of glucose, lactate, and ammonia at the appropriate pH. In such a case, the nutrient concentrations and the pH are set at a media changing interval while considering productivity of the cells. The cell culture media inside the housing is automatically replaced under the control of the level controller. The cell culturing process of the system is performed with an injection of humidified and sterilized gases including oxygen and carbon dioxide into the housing for controlling the pH and dissolved oxygen level of the cells. The system and method of this invention thus automatically performs desired cell culture and analysis.

While the multiple roller tube cell culture system is revolved by the motor, a portion of the bundled cell culture tubes is brought into contact with externally provided cell culture which is then flowed into the culture tubes through the hole of each cell tube. Adhering to the walls of culture tubes, the cells are uniformly distributed owing to the revolution, so that they can be cultured on a large scale in aerobic conditions.

A bundle of the cylindrical culture tubes provide a large inner surface area onto which adherent cells can be grown, so that the cell culture system can take maximal advantage of externally provided oxygen and media to help cells effectively metabolize the carbon sources and nutrients of the media. Under these conditions, lactate is produced in a low quantity with maintenance of constant pH. In addition, with the ability to automatically control the feeding of media and the withdrawal of cultures, the cell culture system of the present invention can culture cells at a high density with high efficiency for a long time. Accordingly, the present invention provides an automatic cell culture system, which affords accurate environmental control to produce proteins of interest at high yield and efficiency.

While a bundle of culture tubes is revolved slowly, a portion of the tube bundle is immersed in a medium filling a lower part of the cell tube housing, so that a culture medium or cell suspension is flowed into each cell tube via two openings which are respectively provided on the opposite sides of the cell tube while being eccentrically located at the corresponding positions in contact with the wall of the cell tube. In the medium, the cells are provided with nutrients and metabolize them. As the shaft is rotated by the motor, the immersed cell tubes emerge from the medium filling the lower part and the medium filling each cell tube comes out through the eccentric openings. Under the aerial condition, the cells remaining in the cell tubes operate their aerobic metabolism pathways. Accordingly, experiencing a nutrient-rich state and aerobic starvation, alternately and repeatedly, the cells adhering to the cell tubes flourish. In the nutrient-rich state, the cells are grown flourishingly. On the other hand, the cells, when subjected to starvation, utilize metabolic pathways for utilizing carbon sources effectively. In this state, the cells produce lactate at a low rate and thus can maintain a constant pH because they are in direct contact with air.

Culture Principle of the Invention

Operated in such a manner that a medium is dispensed into culture tubes and exchanged continuously at a predetermined amount with fresh medium, the cell culture system of the present invention can grow cultures of cells in a batch type manner, a continuous batch type manner, or continuous type manner. With the structure in which air is exchanged through the medium surface within each culture tube, the culture system of the present invention provides large air contact surfaces, compared to conventional culture systems, so that the cells are not under air bubble stress or shear stress, unlike conventional bioreactors.

At cell surfaces in contact with air, effective delivery of air into cells occurs, ensuring smooth glycolysis. In an oxygen-deficient condition, glucose, serving as an energy source, is decomposed into lactic acid to lower medium pH, so that cells are apt to be damaged. On the other hand, in the presence of plentiful oxygen, cells can obtain a large amount of energy through the TCA cycle (tricarboxylic acid cycle) without production of lactic acid which is forced to decrease in pH of the medium. In addition, since glucose, an energy source, is rapidly exhausted at the surface with which cells are in direct contact, cells tend to choose the TCA cycle in order to effectively use carbon sources.

When these conditions are sustained for a long period of time, cells themselves are under stress. Cells can be restored to a normal state if they are placed in a medium so as to bring the cell surface into contact with the medium or are provided with a fresh medium. This principle is used by a roller bottle, which is one of the most popular systems for culturing adherent cells at present. In addition to adopting the same principle, the multiple roller tube of the present invention is improved in air provision and pH control, has significantly small culture spaces, and cultures cells in an automatic operation. Therefore, the culture system of the present invention overcomes the problems that conventional roller bottles have, that is, incapability of automatic operation, air exchange and pH control.

A better understanding of the present invention may be obtained in light of the following examples which are set forth to illustrate, but are not to be construed to limit the present invention.

EXPERIMENTAL EXAMPLE 1
Properties of Culture Systems for Adherent Animal Cells In order to compare the performance and culture properties of the multiple roller tube cell culture system of the present invention with those of other cell culture systems, an measurement was made of cell morphology, percentage of lactate to glucose, cell viability, and culture yield using gene-manipulated CHO cells in flask, roller bottle and bioreactor. The results are given in Table 1, below.

TABLE 1

Culture Properties of Transformed CHO cells According to Culture System

| | Cell | | Bioreactor | |
| --- | --- | --- | --- | --- |
| Property | Culture Flask | Roller Bottle | Microcarrier | Cell cluster |
| Cell Morphology | Monolayer | Monolayer | Monolayer & cluster | Cell cluster |
| Lactate/ Glucose (%) | 70–80 | 40–60 | 90 or more | 95 or more |
| Productivity of Cytokine (unit) | 500–1200 | 1000–2500 | 300–600 | 300 or less |
| Cell Viability | 3 weeks | 4 weeks | 1.5 weeks | Not available |

EXPERIMENTAL EXAMPLE 2
Culture Properties of Transformed C127 Cell According to Culture System Transformed C127 cells were cultured in DMEM with a high content of glucose in a flask, a roller bottle, a bioreactor, and a hollow fiber under various conditions while observing cell morphology, growth location, recombinant viral protein, and culture period. The results are given in Table 2, below.

TABLE 2

Culture Properties of Transformed C127 Cell According to Culture System

| | Flask | Roller Bottle | Bioreactor | Hollow fiber |
| --- | --- | --- | --- | --- |
| Medium | DMEM | As left | As left | As left |
| Cell morphology at production | Multilayer fiber | As left | Multilayer fiber/clustered | Clustered |
| Matrix | Polystyrene | Polystyrene | Dextran | Cell itself |
| Culture Type | Batch | Batch | Batch (STR) perfusion | Continuous |
| Control | 5% $CO_2$ | None | 4 gases controlled | 2 gases exchanged |

TABLE 2-continued

Culture Properties of Transformed C127 Cell
According to Culture System

|  | Flask | Roller Bottle | Bioreactor | Hollow fiber |
|---|---|---|---|---|
| Growth locus | Flask bottom in medium | Wall, in & out medium | Surface in medium | Fiber surface in medium |
| Lactate/Glucose | ≈70% | ≈0–50% | ≧95% | ≈100% |
| Productivity (viral protein) | 1–2 mg/L | 6–12 mg/L | 0.1–0.3 mg/L | 0.01–0.03 mg/L |
| Cell Viability | 1 month | 3 months | Not available | Not available |

As seen in Tables 1 and 2, the productivity of recombinant viral proteins varies with culture systems. It is believed that the increased productivity and extended cell viability of the roller bottle is attributed to the fact that oxygen is smoothly fed to the cell membranes from the air within roller bottle, temporary exhaustion of carbon sources allows the cells to effectively use the carbon source remaining, and cells are transferred into the medium to absorb a sufficient amount of nutrients. In the flask, cells are grown in the medium, adhering to the bottom. This culture system is efficient while cells grow at a low density. However, it is not easy for oxygen to penetrate into the medium contained in a flask. Further, the cycle from supernutrition to in nutrition (that is, medium exchange cycle) is long so that the cells are liable to be damaged by high cell density, in addition to having difficulty in efficiently using carbon sources. On the other hand, when culturing is carried out with microcarriers serving as a matrix or cells being suspended, dissolved oxygen levels are increased. In this case, however, the cells undergo changes in cell morphology so that carbon sources cannot be efficiently utilized, reducing the productivity. Particularly, the lactate thus produced acidifies the medium, making the medium exchange cycle shorter. Further, desired biomaterials produced as a result of gene manipulation are generally vulnerable to low pH, which results in reducing the productivity.

EXAMPLE 1

To test the performance of the multiple roller tube cell culture system of the present invention, $CHO^{dhfr-}$ cells, which are most widely used for the production of cytokines, were used. Before culturing, inner surfaces of the culture tubes were coated with a 2 % gelatin solution (Sigma G1393) for 2 hours to facilitate cell adherence. For comparison, a tissue culture flask made of polystyrene (equipped with a 0.2 μm filter cap having 75 $cm^{2,}$ Corning #430641) was also used. For use in this experiment, a culture medium based on Isocove's modified Dulbecco's medium (Gibco Cat. No. 12200-036) containing 3.024 g/L of $NaHCO_3$ was based. In addition, the medium was added with HT (hypoxantin thymidine supplement, Gibco Cat. No. 11067-030) and supplemented with fetal bovine serum (FBS, Gibco Cat. No. 26140-079) at an amount of 10 % by volume. The multiple roller tube cell culture system was composed of 17 cell tubes with a total inside area of 694 $cm^{2,}$ CHO cells were suspended at an initial density of $4 \times 10^7$ cells in 200 ml of the medium and cultured on a roller drum within an incubator (37° C.) with the culture system being sealed. In the case of the flask, the cells were suspended at a density of $4.322 \times 10^6$ cells in 22 ml of the medium and the suspension was added into the flask, followed by culturing in a 5 % $CO_2$ incubator. 48 hours after the initial suspending of cells, the medium was exchanged with a fresh one. Thereafter, medium exchange was carried out every 48 hours while measuring glucose and lactate levels with an assay kit (Sigma). The drawn media were measured to maintain pH at 7.0 or higher. The cell culture system was revolved at a speed of ⅓-¼ rpm.

Within 24 hours from the addition of the cell suspension into the cell tubes, cells were desirably attached to the inside walls of the cell tubes. The cells were still found to maintain their adherence to tube walls even after 1 month of the culturing, as measured by crystal violet dying. A predetermined volume of a fresh culture medium was fed into the cell tubes to replace the same volume of the used medium by the revolution of the culture system, which was confirmed to be normally operated at up to 30 rpm. When the medium rapidly decreased in pH as the culture period was extended, feeding fresh air restored pH values to a normal state with ease. The attachment behavior and morphology of cells grown in the cell tubes were not significantly different from those of cells grown in the tissue culture flask. However, the time period that it took for the cells to adhere completely to the wall of the cell tubes was measured to be 24 hours, which was 8 hours longer than the attachment time period in the flask. Cell growth could be identified directly through a microscope and indirectly by the analysis of metabolites.

From these culture results, it was seen that the cell culture system could be operated in an automatic manner because the medium continually fed to the lower part of the cell system flowed into or out of the cell tubes as the cell culture system revolved. Employment of culture tubes made of plastic (i.e., polystyrene) brought about an improvement in cell adherence. Even in the case of cell suspension, carbon sources could be effectively utilized through environmental control in the cell culture system. When materials capable of collecting cells within cell tubes were inserted or attached to the cell tubes, the suspended cells could be grown.

EXAMPLE 2

In the automatic multiple roller tube cell culture system of the present invention, cells pretreated as in Example 1 were cultured for a long period of time. First, the culture medium was transferred at a predetermined amount from the reservoir to the culture system through the inlet with the aid of the pump and the level controller. The motor, which was connected through the axis to the cell tube bundle, was revolved at a speed of 1.0 rpm or less to bring the cell tubes into contact with the medium, thereby culturing the cells. Culture conditions were controlled with monitoring of the pH and dissolved oxygen level of the medium by use of a sensor. After being measured for concentration, the medium was exchanged with a fresh one while the revolution speed was increased to 60 rpm or less. Throughout the culture period, the cells were attached to the wall and grown without difficulty. In addition, medium exchange was conducted smoothly in the cell culture system. A pH increase took place upon medium exchange, but provision of $CO_2$ returned the pH to a normal state. That is, the pH of the medium could be controlled by the provision of air during cultivation. Accordingly, it was seen that two-gas environment control was possible.

Figure 5:
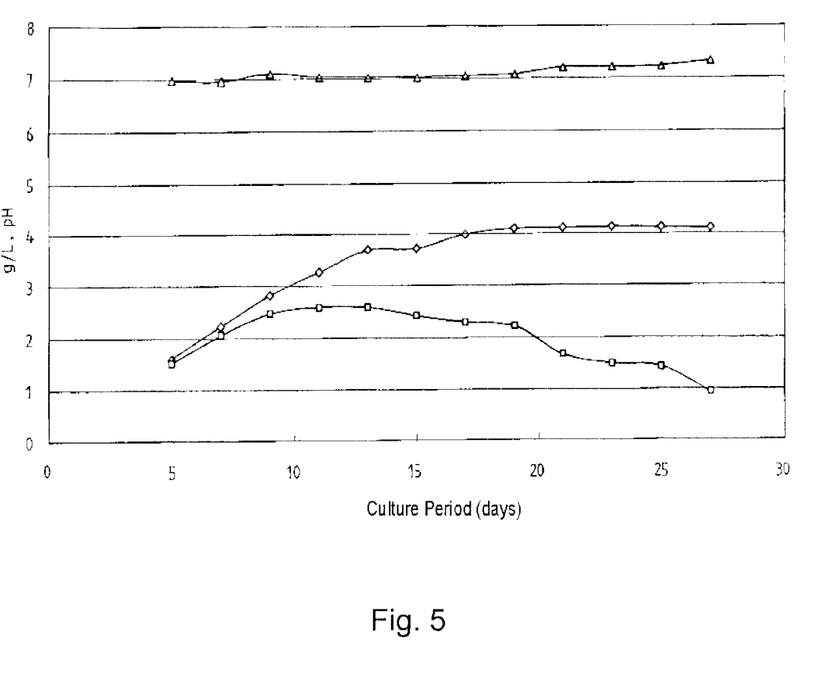
FIG. 5 is a graph in which the pH (-Δ-), consumed glucose (-◇-), and produced lactate (-□-) of a cell culture are plotted versus culture period when the cell culture is grown in the multiple roller tube cell culture system.
Figure 7:
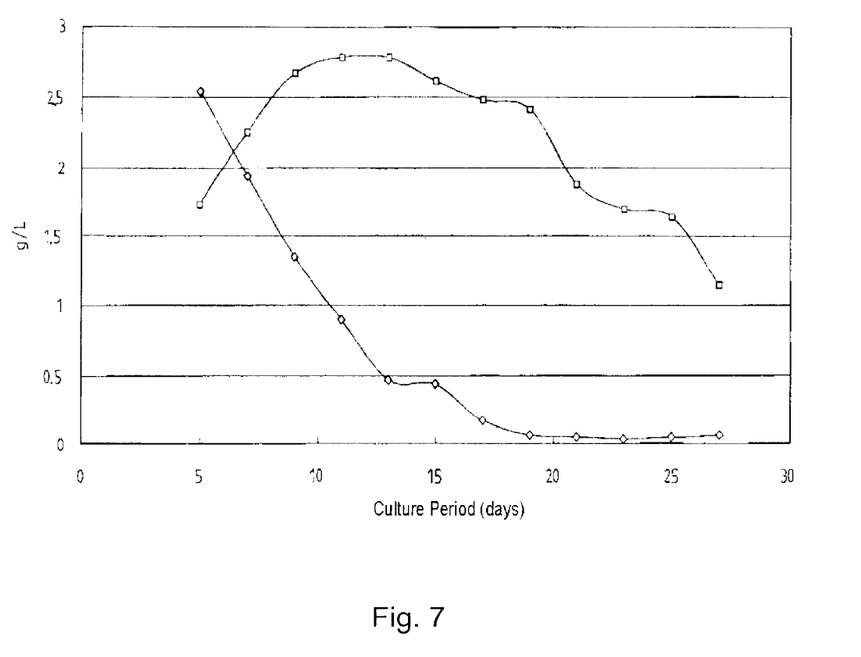
FIG. 7 is a graph in which levels of glucose (-◇-) and lactate (-□-) in the medium are plotted versus culture period when the cell culture is grown in the multiple roller tube cell culture system.

With reference to FIGS. 5 and 7, there are shown the relationships between glucose absorption and lactate production and between medium glucose and lactate levels, respectively, in the culture system of the present invention. Able to utilize carbon sources of the culture medium as proved by a decrease in the production of lactate in comparison to the amount of glucose consumed in FIGS. 5 and 7. These results indirectly indicate that cell culture system could produce cytokines at high yields. Therefore, increasing the number of culture tubes allows cells to be cultured in a mass scale.

Cells were firmly attached to the inside walls of the cell tubes as in Example 1 and this attachment was still maintained even after 1 month of cultivation. The revolution of the cell culture system fed a predetermined volume of a fresh medium into the cell tubes while drawing the same volume of the used medium. The pH of the medium was decreased as cells were grown to produce lactate. However, the pH of the medium could be normalized easily by providing air.

Figure 6:
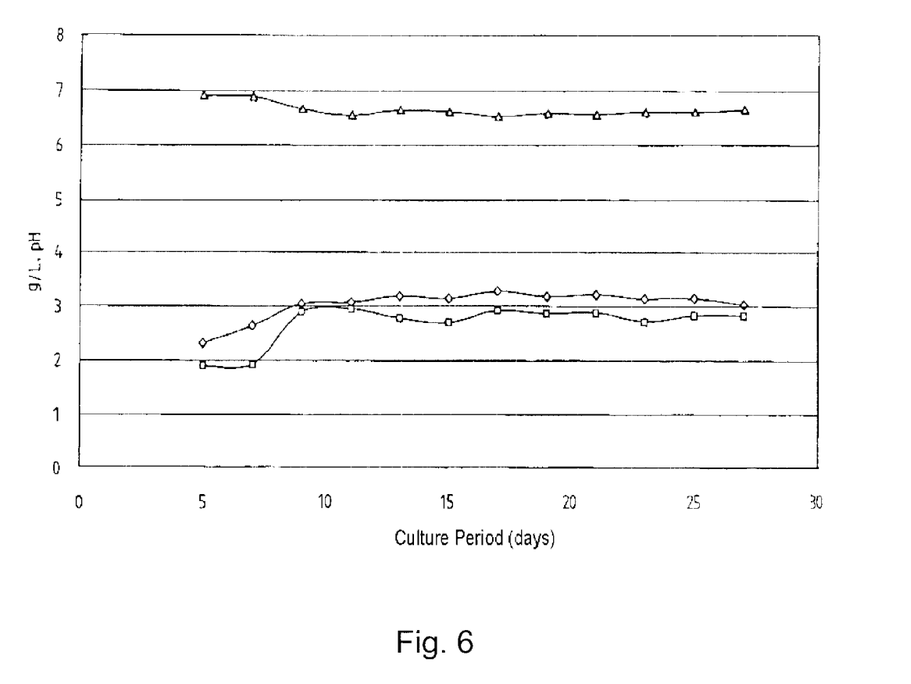
FIG. 6 is a graph in which the pH (-Δ-), consumed glucose (-◇-), and produced lactate (-□-) of a cell culture are plotted versus culture period when the cell culture is grown in a tissue culture flask.
Figure 8:
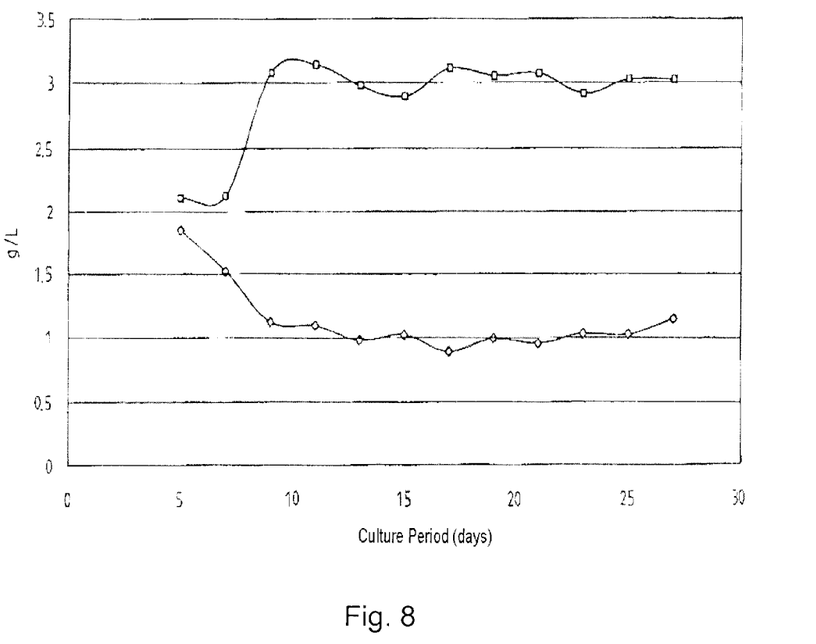
FIG. 8 is a graph in which levels of glucose (-◇-) and lactate (-□-) in the medium are plotted versus culture period when the cell culture is grown in the tissue culture flask system.

From the initiation, the culture was monitored for 27 days. When being cultured in the cell culture system, the cells were observed to be improved in metabolism until the $19^{th}$ day as measured for glucose uptake ratio (FIGS. 5 and 7). On the other hand, when the cells were cultured in the flask, the cell metabolism was not further improved from the $9^{th}$ day with glucose level remaining at about 100 mg/dl (FIGS. 6 and 8). Lactate was produced at increasing amounts until the $13^{th}$ day after providing fresh air at the $9^{th}$ day in the cell culture system. Compared with the glucose consumed, however, the lactate production can be said to be decreased rather than increased. In fact, the ratio of produced lactate to consumed glucose was reduced to as low as about 22.9 % (FIGS. 5 and 7). In contrast, the lactate production was measured to remain at 300 mg/dl from the $9^{th}$ day in the flask culture, which corresponded to 90 % of the amount of absorbed glucose (FIGS. 6 and 8). Since the $19^{th}$ day, the revolution speed was reduced to ¼ rpm from ⅓ rpm in the cell culture system. As a result, the ratio of produced lactate to consumed glucose was significantly lowered, indirectly demonstrating the starvation effect of utilizing carbon sources with efficiency.

As for the pH of the medium, it was reduced to 6.98 in the cell culture system before feeding fresh air in the early stage and maintained at 7.0 or higher after feeding fresh air. When the cell culture system was revolved at ⅓ rpm to utilize carbon sources effectively, the medium was measured to have pH 7.00–7.07. At ¼ rpm, the pH value was increased to 7.20–7.32, providing an optimal condition for the growth of animal cells (FIG. 5). By contrast, no starvation effects could be observed from the culture in the flask. From the $5^{th}$ day, the medium of the flask was measured to range, in pH, from 6.50 to 6.90 (FIG. 6), which negatively affects cell culture, especially the production of cytokines of interest.

As described hereinbefore, the cell culture system of the present invention makes cells adhere to the wall of cell tubes and provides air directly to cell surfaces. Accordingly, adherent cells can be grown with normal morphology at high yield for a long period of time in the cell culture system. Additionally, cell culture can be easily scaled up simply by increasing the number of the roller drums or enlarging the assembly of cell tubes. Further, the cell culture system of the present invention enjoys the advantage of being capable of exchanging media and feeding a gas mixture of oxygen and carbon dioxide easily, thereby providing optimal environments suitable for small to large scale cell culture.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A cell tube for use in culturing cells, having two openings through which culture media can come in and out, said openings being eccentrically located on opposite end walls at corresponding positions in contact with the edge sides of the end walls.

2. The cell tube as set forth in claim 1, wherein the cell tube has a cross sectional shape selected from the group consisting of circles, ellipses, and polygons .

3. The cell tube as set forth in claim 1, wherein the cell tube ranges, in length, from 10 to 300 mm and, in diameter, from 5 to 110 mm.

4. The cell tube as set forth in claim 1, wherein the openings have a shape selected from the group consisting of circles, ellipses, and polygons and occupy an area of 1 to 70% based on the total area of the end walls.

5. The cell tube as set forth in claim 1, wherein the openings are means serving as an inlet and an outlet of culture media.

6. A multiple roller tube cell culture system, comprising:
one or more cell culture tube bundles, each consisting of a plurality of cell culture tubes axially arranged around a central rotating shaft within a cylindrical housing such that an eccentric hole formed on each end wall of each of said tubes is positioned outward in a radial direction of the axis of the housing;
an air inlet and an air outlet formed on said housing for feeding oxygen to the interior of said housing;
a level controller for maintaining a desired level of cell culture medium inside the housing;
a medium inlet for feeding the cell culture medium to the interior of said housing;
a sensor for sensing the pH and dissolved oxygen level inside the housing; and
a harvest outlet for automatically discharging culture products from the housing after the cell culturing process is finished.

7. The multiple roller tube cell culture system as set forth in claim 6, wherein the tubes are arranged inside the housing such that the holes of the tubes are positioned outward in a centrifugal direction of the housing, thus allowing the cell culture medium to smoothly flow into or from the tubes.

8. The multiple roller tube cell culture system as set forth in claim 6, wherein the cell culture medium flows into or from the tubes through the holes due to gravity.

9. The multiple roller tube cell culture system as set forth in claim 7, wherein said cell culture tubes are arranged parallel to the centrifugal direction or inclined from the centrifugal direction at an angle of 0–10° to accomplish a desired flow of the medium relative to the tubes.

10. The multiple roller tube cell culture system as set forth in claim 7, wherein said cell culture tube bundles are arranged parallel to each other in the system.

11. The multiple roller tube cell culture system as set forth in claim 6, wherein said cell culture tubes are made of glass or plastic.

12. A method for culturing adherent animal cells in a mass scale using the multiple roller tube cell culture system of claim 6, comprising the steps of:

feeding a predetermined amount of a culture medium into the cell culture system through the inlet by use of the medium transfer pump under the control of the level controller;

rotating the roller drum on which cell tubes are assembled, bring a portion of cell tubes into contact with the influent medium and air, said cell tube assembly being connected to the axis of the motor;

controlling the pH and dissolved oxygen level of the cell culture with the aid of sensors; and replacing the cell culture with a fresh medium and recover the cell culture.

13. The method as set forth in claim 12, wherein the cell tubes are coated with a gelatin solution at their inside surfaces or contain fibers or spongy therein to facilitate the attachment of cells.

14. The method as set forth in claim 12, wherein the controlling step is carried out by feeding sterile moisture gas mixture of oxygen and carbon dioxide in proportions with 90:10 to 100:0.

* * * * *